(12) United States Patent
Notton et al.

(10) Patent No.: US 11,510,406 B2
(45) Date of Patent: Nov. 29, 2022

(54) IONISER EQUIPPED WITH AN IONIC FLOW ACCELERATOR IN PARTICULAR TO PROTECT AGAINST MOSQUITOES

(71) Applicant: ANCILIA PROTECT LTD, London (GB)

(72) Inventors: Philippe Notton, Roche-la-Moliere (FR); Christophe Giovannetti, Chambourcy (FR); Salah Eddine Lamamri, Chambourcy (FR)

(73) Assignee: ANCILIA PROTECT LTD, Londres (GB)

( * ) Notice: Subject to any disclaimer, the term of this patent is extended or adjusted under 35 U.S.C. 154(b) by 298 days.

(21) Appl. No.: 16/759,856

(22) PCT Filed: Oct. 24, 2018

(86) PCT No.: PCT/EP2018/079158
§ 371 (c)(1),
(2) Date: Apr. 28, 2020

(87) PCT Pub. No.: WO2019/081580
PCT Pub. Date: May 2, 2019

(65) Prior Publication Data
US 2020/0305411 A1 Oct. 1, 2020

(30) Foreign Application Priority Data
Oct. 28, 2017 (FR) ...................................... 1771136

(51) Int. Cl.
*A01M 29/28* (2011.01)
*H01T 19/00* (2006.01)
*H01T 23/00* (2006.01)
(52) U.S. Cl.
CPC ............. *A01M 29/28* (2013.01); *H01T 19/00* (2013.01); *H01T 23/00* (2013.01)

(58) Field of Classification Search
CPC ........ A01M 29/28; H01T 19/00; H01T 23/00; Y02A 50/20; F24F 8/30; F24F 8/192;
(Continued)

(56) References Cited

U.S. PATENT DOCUMENTS 5,268,009 A 12/1993 Thompson et al.
9,754,757 B2 * 9/2017 Nishida ................. H01J 27/022
(Continued)

FOREIGN PATENT DOCUMENTS

| EP | 0 048 102 A1 | 3/1982 |
| WO | WO 2012/114674 A1 | 8/2012 |
| WO | WO 2017/038111 A1 | 3/2017 |

OTHER PUBLICATIONS

WO-2017-038111; Hiromu Nishida; Ion generator device, method for producing ion generation device, and electrical device; Drawings and Specification (Year: 2017).*
(Continued)

*Primary Examiner* — Dharti H Patel
(74) *Attorney, Agent, or Firm* — Pillsbury Winthrop Shaw Pittman LLP (57) ABSTRACT

A device for ionising air includes a case, in which there are a blower, which includes a rotor to generate a pulsed airflow and an exhaust pipe to channel this flow; a device for producing ions, which includes a high-voltage electrical generator; an electrode connected to the generator and of which one free end, formed of a cluster of filaments made of conductive material, extends to the right of the exhaust pipe to release ions there by corona discharge. The device further includes a diffuser provided with a pipe which, in the extension of the exhaust pipe, delimits a compression chamber, with an expander which extends the pipe and includes a series of channels which extend form an inner face of the expander to an opposite outer face.

9 Claims, 5 Drawing Sheets

(58) Field of Classification Search
CPC .......... F24F 7/00; A61L 9/22; A61L 2209/11; A61L 2209/134; A61L 2209/16
USPC .......................................... 361/231
See application file for complete search history.

(56) References Cited

U.S. PATENT DOCUMENTS

| | | | | |
|---|---|---|---|---|
| 2007/0103842 A1* | 5/2007 | Partridge | ................ | H01T 23/00 361/220 |
| 2010/0033891 A1* | 2/2010 | Orihara | ................... | H01T 23/00 361/231 |
| 2011/0150697 A1* | 6/2011 | Okano | ................. | F24F 1/0071 422/4 |
| 2012/0207647 A1* | 8/2012 | Kim | ........................ | A61L 9/00 422/107 |
| 2013/0120895 A1* | 5/2013 | Lai | ...................... | B60H 3/0071 361/231 |
| 2015/0078964 A1* | 3/2015 | Meirav | ............. | B01J 20/28035 96/144 |
| 2016/0102589 A1* | 4/2016 | Kim | ........................ | B03C 3/88 96/65 |
| 2017/0007953 A1* | 1/2017 | Lee | ........................ | B03C 3/368 |
| 2020/0054780 A1* | 2/2020 | Ezaki | ..................... | A61L 9/122 |

OTHER PUBLICATIONS

International Search Report as issued in International Patent Application No. PCT/EP2018/079158, dated Jan. 31, 2019.

* cited by examiner

IONISER EQUIPPED WITH AN IONIC FLOW ACCELERATOR IN PARTICULAR TO PROTECT AGAINST MOSQUITOES

CROSS-REFERENCE TO RELATED APPLICATIONS

This is the U.S. National Stage of PCT/EP2018/079158, filed Oct. 24, 2018, which in turn claims priority to French Patent Application No. 1771136, filed Oct. 28, 2017, the entire contents of all applications are incorporated herein by reference in their entireties.

The invention relates to the field of ionisers.

Ionisers are commonly used to purify air. The principle, quite simple, is based on corona discharge: one (or more) electrode(s) connected to a high-voltage (and low intensity) electrical source cause the ionisation of the surrounding environment, accompanied by electrical discharges.

In practice, the electrode can be formed (at least at one free end) of very fine filaments (for example, made of glass or carbon fibre, treated to be conductors of electricity). These filaments are placed in an airflow generated by blowing, which removes ions.

The ions are coupled with the particles suspended in the air, that by burdening, they contribute to flattening to the ground.

A typical ioniser using this technology is described in U.S. Pat. No. 5,268,009.

It has recently been discovered that an ioniser can contribute to warding off insects (and in particular, diptera) usually attracted by body odours (in particular, female mosquitoes). Indeed, these body odours are carried by particles (in particular, perspiration), that it proves to be possible to flatten to the ground by coupling to the ions coming from an ioniser.

In other words, it is possible by means of an ioniser to permanently deodorise the individual (or the animal) exposed to insects (in particular, mosquitoes). Made, in any way, invisible to these, the individual (or the animal) is protected from their strings (or bites).

Ionisers have been proposed for wearing on the neck or on the wrist. Wearing them is however limited and cannot protect several individuals simultaneously.

To increase the wearing of an ioniser, the simplest is to increase the power of the blowing. But, this results in an increase in the electrical consumption of the ioniser, incompatible in particular with an extended use when travelling or in regions with no mains electric supply.

A first aim of the invention is consequently to propose an ioniser of which the scope is increased, while having a moderate electrical consumption.

A second aim of the invention is to propose an ioniser making it possible to diffuse ions in a significant volume, in particular for the purpose of making, in this volume, individuals invisible in the olfactory sense of insects, and in particular mosquitoes.

For this purpose, an air ionisation (ioniser) device is proposed, which comprises a case and, in this case:
  A blower, which includes a rotor for generating a pulsed airflow and an exhaust pipe to channel this flow;
  A device for producing ions, which comprises:
  A high-voltage electrical generator;
  At least one electrode connected to the generator, and of which a free end, formed of a cluster of filaments made of conductive material, extends to the right of the exhaust pipe to release the ions there by corona discharge;
  A diffuser provided:
    With a pipe which extends into the extension of the exhaust pipe and delimits a compression chamber, and
    With an expander which extends the pipe and comprises a series of channels which extend from an inner face of the expander adjoining the compression chamber to an opposite outer face.

The diffuser has the effect of accelerating the airflow which passes through it, for the benefit of the scope (and therefore the effectiveness) of the ioniser.

Various additional features can be provided, individually or in combination. Thus, for example:
  The channels will be extended from one another from the inner face of the expander to the outer face thereof.
  Each channel will be narrowed from the inner face of the expander to the outer face thereof.
  The ioniser comprises a metal ring surrounding the free end of the electrode.
  The metal ring has a flared portion (in particular, of the conic or pyramid shape) which surrounds the cluster of filaments of the electrode.
  The metal ring is crimped on the electrode.
  The metal ring is made of copper.
  The metal ring is silver on the surface.
  The case comprises a base and a cover provided with perforation at least to the right of the diffuser.
  The ioniser comprises an electronic control board provided with a switch for opening or closing an electrical supply circuit of the generator, and the case is provided with a pushbutton coupled with the switch.

Other aims and advantages of the invention will appear in light of the description of an embodiment, made below in reference to the appended drawings, wherein.

Figure 1:
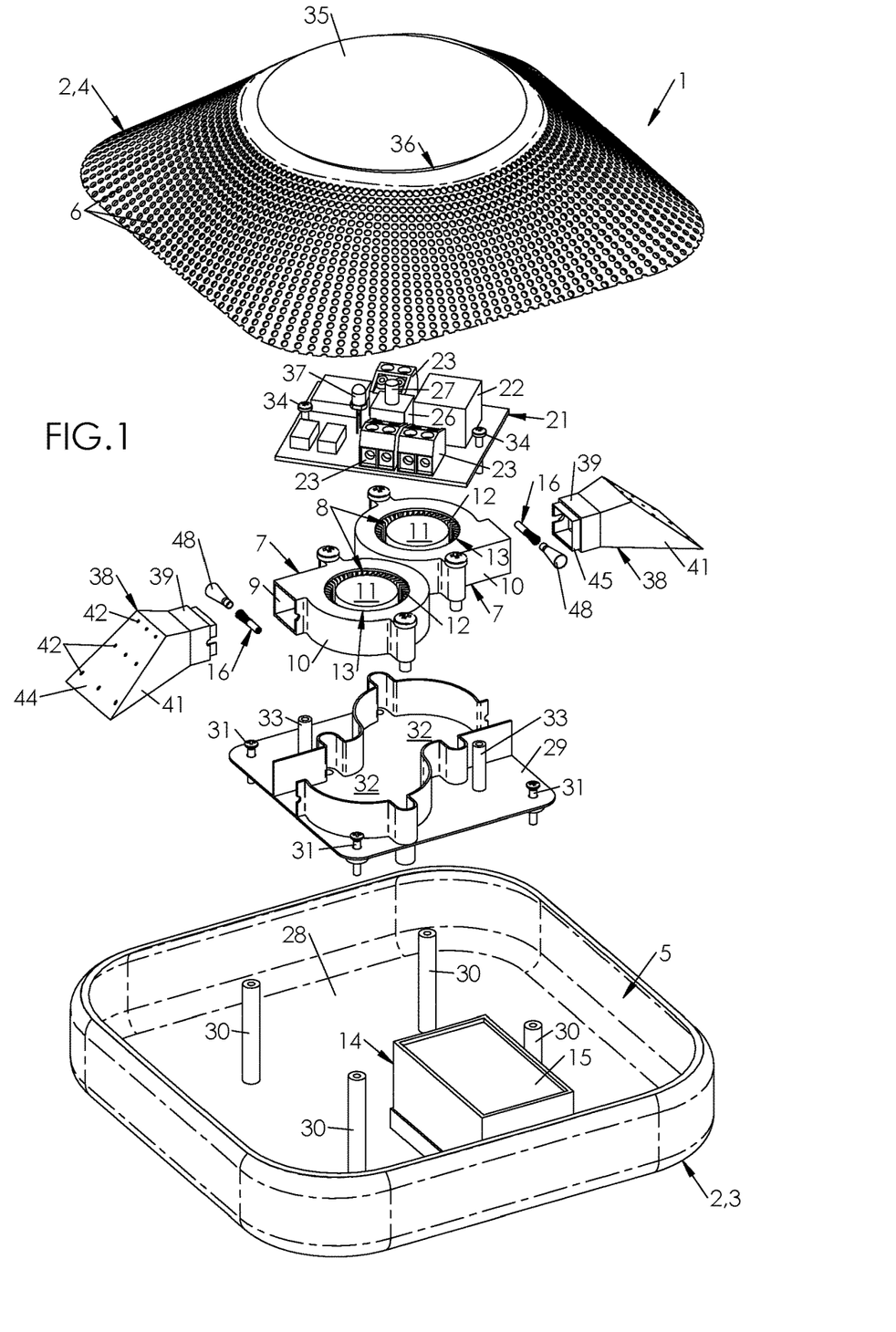
FIG. 1 is an exploded, perspective view showing an air ionisation device.

In FIG. 1, an air ionisation device is represented, below more simply called ioniser 1. This ioniser 1 is designed to produce one or more pulsed ion flows, intended to be associated with particles suspended in the air of opposed electrical charge.

The molecules (or molecule groups) formed by the association of pulsed ions and particles are heavy and, under the effect of the weight thereof, flattened to the ground.

The ioniser 1 is advantageously designed to generate negative ions (anions), typically $CO_3$ ions. Below, it will be shown how.

The ioniser 1 comprises, first, a case 2.

In the example illustrated, the case 2 comprises a base 3 and a cover 4.

The base 3 can rest on a support (for example, a table), to be fastened to a wall or a partition (surface-mounted), or also to be fastened to a ceiling (ceiling-mounted).

In the example illustrated, the base 3 has a substantially square edge (with preferably rounded corners).

The cover 4 is advantageously pyramidal, with a complementary base of the edge of the base 3.

Together, the base 3 and the cover 4 define an inner volume 5 wherein various components of the ioniser 1 are arranged.

The cover 4 is provided with perforations 6. These perforations 6 are intended to make it possible for the passage of air through the cover 4.

The ioniser 1 comprises, second, at least one blower 7. This blower 7 comprises a rotor 8 to generate a pulsed airflow, and an exhaust pipe 9 to channel this flow.

In the example illustrated, the blower 7 is presented in the form of a ventilator. The blower 7 comprises, in this case, a box 10 (here, cylindrical) wherein the rotor 8 is mounted pivoting. The box 10 carries a stator (not represented) supplied with current, and designed to generate a rotating magnetic field, rotating the rotor 8.

In the example illustrated, the rotor 8 comprises a shaft 11 and a plurality of peripheral blades 12 integral with the shaft 11 and which, during the rotation of the rotor 8, generating the airflow.

According to a preferred embodiment illustrated in FIG. 1, the ioniser 1 comprises two blowers 7. The blowers 7 are, for example, mounted back-to-back, i.e. that the flows generated are pulsed in opposite directions.

As illustrated, in particular, in FIG. 1, the box 10 is provided with an air inlet (here, formed by an opening 13 just under the rotor 8).

The exhaust pipe 9 is here formed by an opening made on a side of the box 10. In the example illustrated, the exhaust pipe 9 has a rectangular (or square) cross-section, but it could be a circular or oval cross-section.

The ioniser 1 comprises, third, a device 14 for producing ions, which comprises:

A high-voltage electrical generator 15;

At least one electrode 16 connected to the generator 15 and of which one free end 16, formed of a cluster of filaments 18 made of conductive material, extends into the exhaust pipe 9 to release ions there by corona discharge.

The high-voltage generator 15 is connected to an electrical voltage source (for example, a battery, a cell, or the mains—via a transformer). The generator is designed to produce high-voltage electricity (several thousand volts, even several tens of thousands of volts) and low intensity (a few milliamps, even a few microamps).

In the example illustrated, where the ioniser 1 comprises two blowers 7, the device 14 for producing ions comprises two electrodes 16, each associated with a blower 7.

Figure 2:
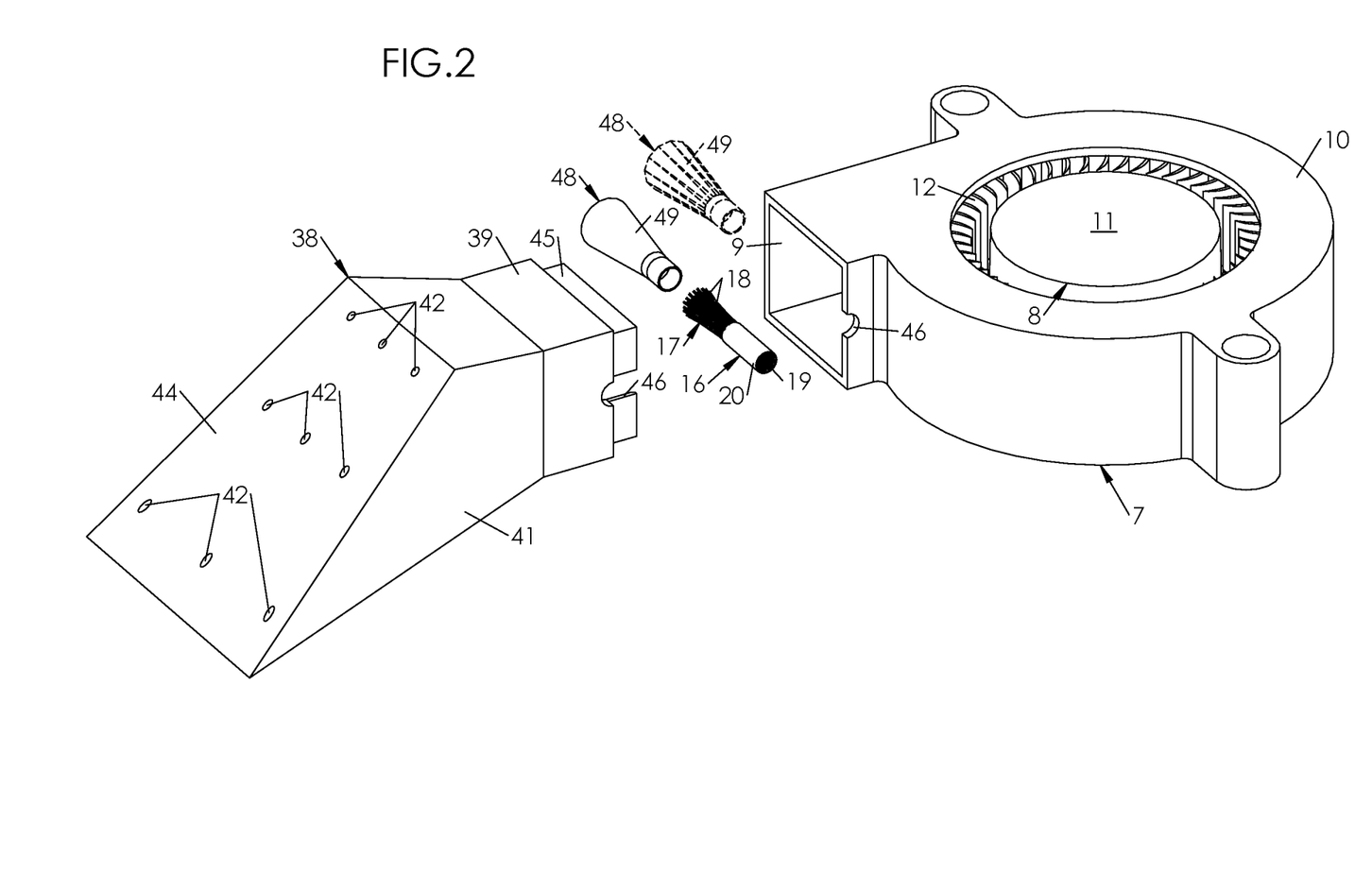
FIG. 2 is an exploded, perspective view showing a blower and the associated diffuser thereof.

Each electrode 16 comprises a conductor 19 connected to the generator. To minimise losses, the conductor 19 is, over at least some of the length thereof, surrounded by a sleeve 20 (for example, made of a flexible insulating polymer). As can be seen in FIG. 2 and in FIG. 3, the free end 16 of the electrode (i.e. the cluster of filaments 18) is stripped.

Figure 3:
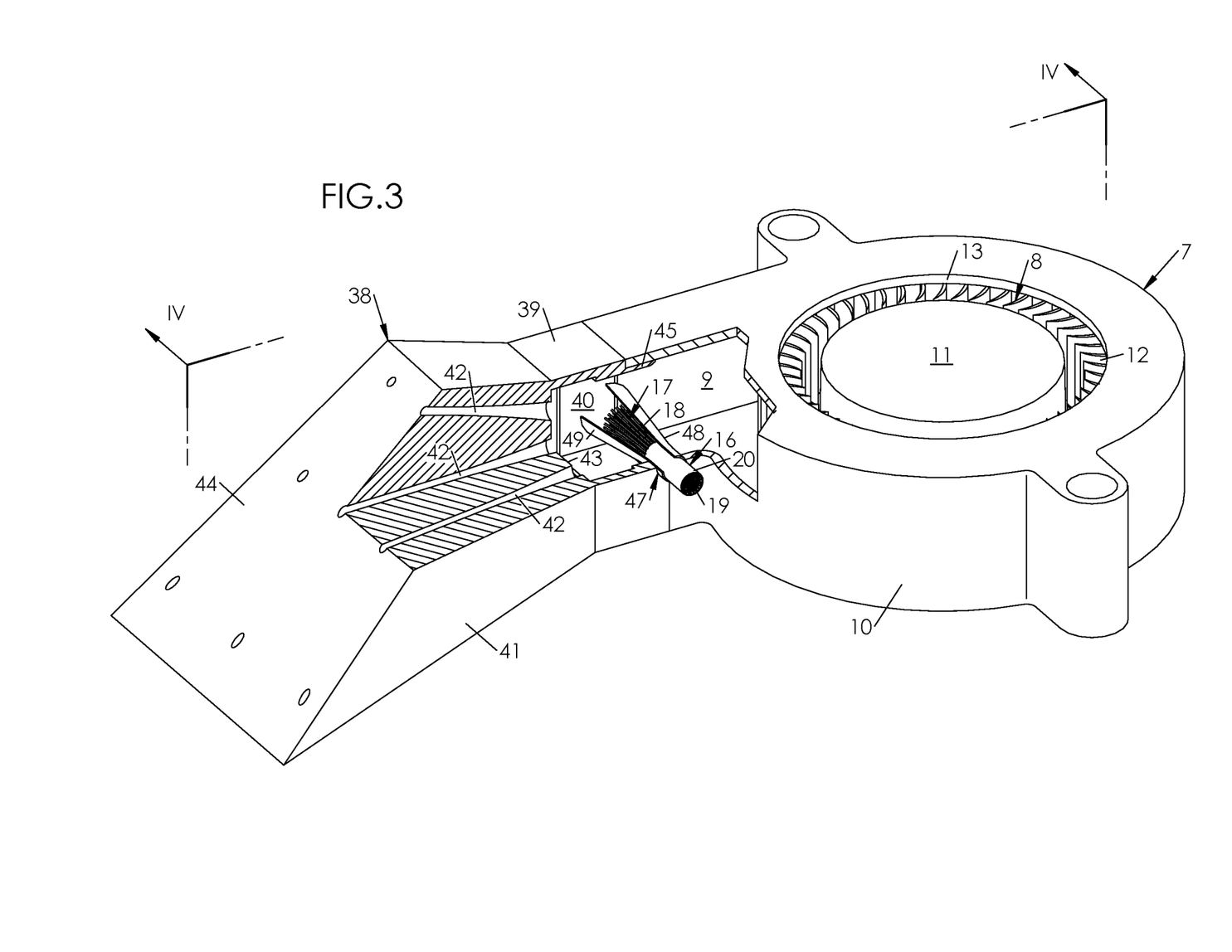
FIG. 3 is a partial, extracted view showing the blower and the diffuser thereof assembled.
Figure 4:
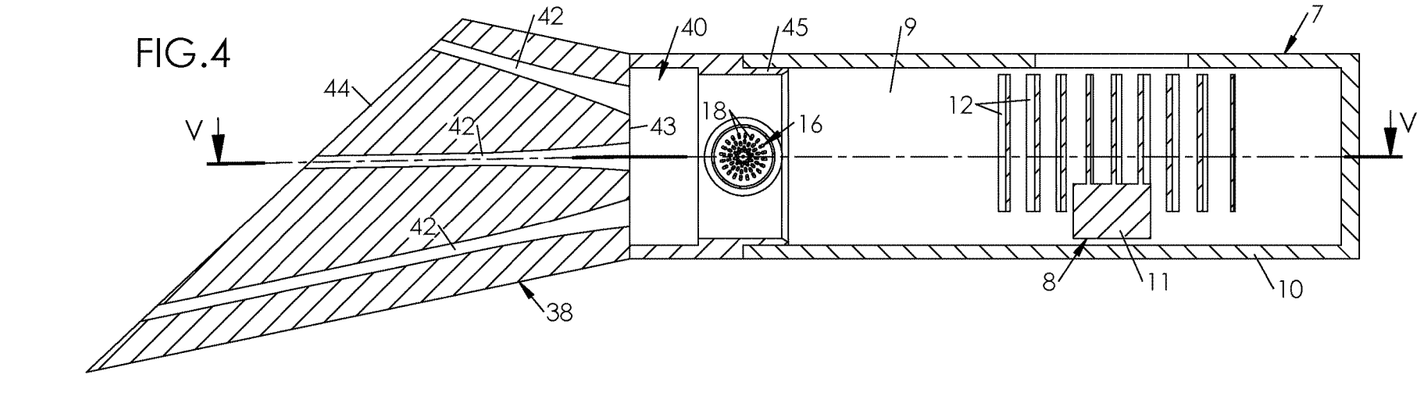
FIG. 4 is a cross-sectional view of the blower and of the diffuser, along the cross-sectional plane IV-IV of FIG. 3.

The filaments 18 can together constitute the conductor 19 over the whole of the length thereof, or only form a portion of the conductor 19 by being connected to a wire (for example, metal), itself connected to the generator 15.

Figure 5:
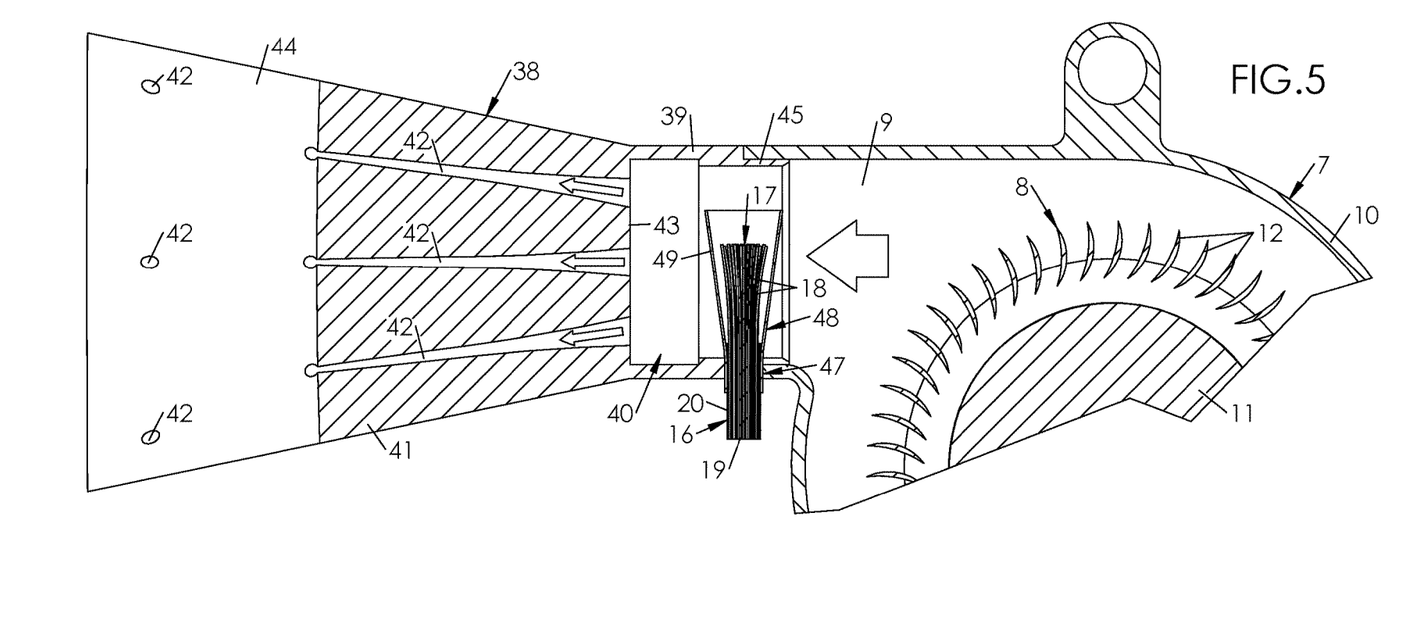
FIG. 5 is a cross-sectional view of the plane V-V of FIG. 4.
Figure 6:
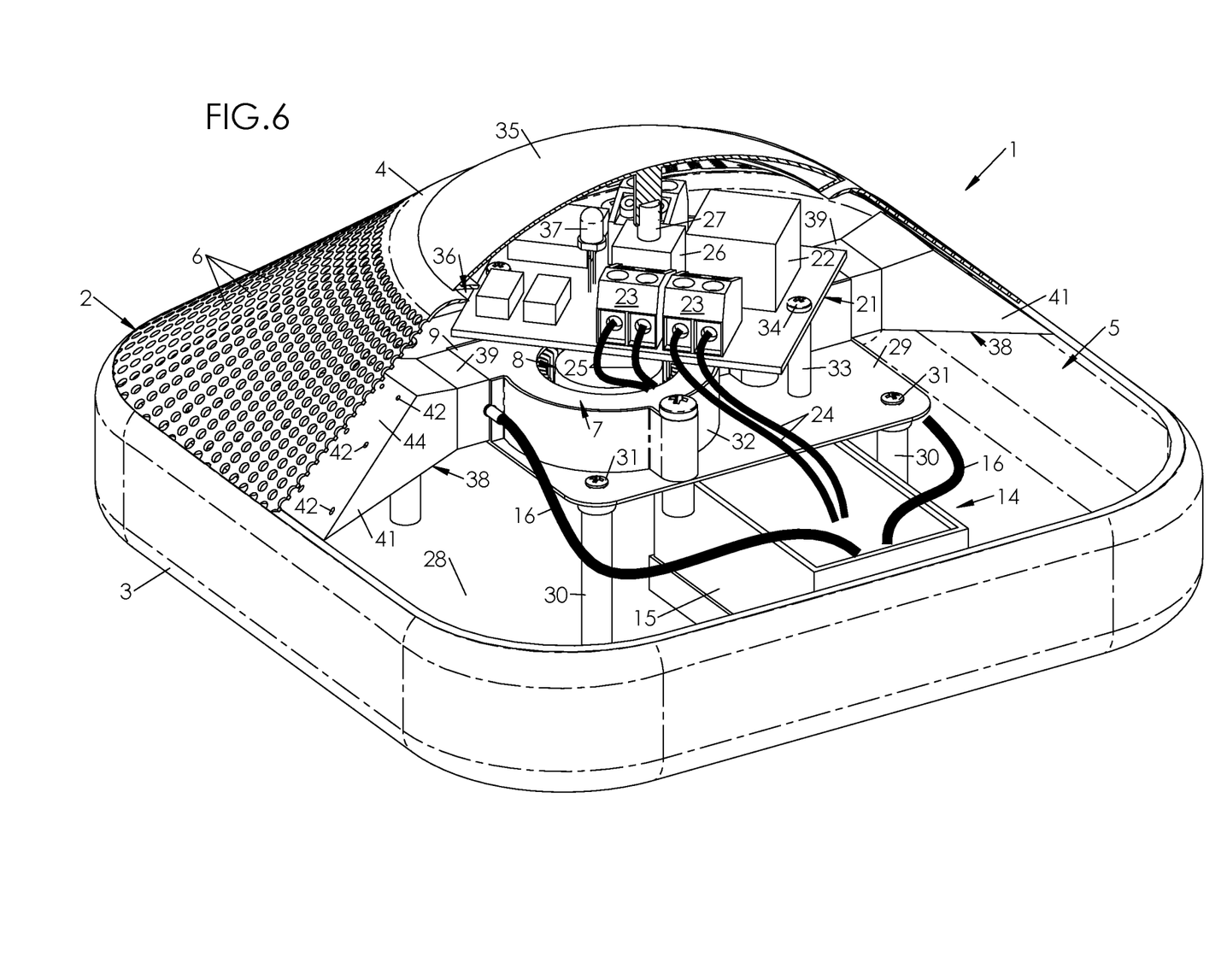
FIG. 6 is a partial, extracted view showing the assembled ionisation device.

As can be seen in FIG. 1 and in FIG. 5, the ioniser 1 comprises, fourth, control electronics, in the form of an integrated circuit board 21 including electronic components and forming a circuit for electrically supplying the generator 15.

In the example illustrated, the board 21 comprises a transformer 22, designed to generate an average voltage (of around 12 V) intended to supply the other components and to be supplied with the high-voltage generator 15.

The board 21 also comprises terminals 23, on which are connected conductors 24 for electrically supplying the generator 15, as well as conductors 25 for electrically supply the (or each) blower 7. More specifically, the latter electrical conductors 25 are connected to the stator of each blower 7.

The switching on of the ioniser 1 can be controlled remotely, for example, by means of a remote control (infrared or radiofrequency), or by means of a remote switch mounted on a circuit for electrically supply the ioniser 1.

The switching on of the ioniser 1 can also be carried out by direct action on it. Thus, according to an embodiment illustrated in FIG. 1 and FIG. 5, the board 21 is provided with a switch 26 for opening or closing the circuit for electrically supplying the generator 15.

This switch 26 comprises, for example, a rod 27 mounted in translation between a high position, wherein the circuit is open (the generator 15 and each blower 7 thus having no electrical supply) and a low position, wherein the circuit is closed (the generator 15 and each blower 7 thus being electrically supplied).

From an architectural standpoint, as illustrated in FIG. 1 and in FIG. 5, the generator 15 is mounted on a bottom wall 18 of the base 3. The (or each) blower 7 is mounted on a plate 29 (made, for example, of a plastic material). This plate 29 is fixed on the base 3. In the example illustrated, the plate 29 is mounted on funnels 30 which protrude from the bottom wall 28 of the base 3. The fixing of the plate 29 on the funnels 30 is, for example, carried out by means of screws 31.

As illustrated in FIG. 1, each blower 7 is slotted in a complementary housing 32 formed protruding on the plate 29. The fixing of each blower 7 on the plate 29 is, for example, carried out by means of screws.

According to a preferred embodiment illustrated in FIG. 1 and in FIG. 5, the electronic board 21 is mounted on top of the blower(s). To this end, the board 21 is mounted on pins 33 which protrude from the plate 29. The fixing of the board 21 on the pins 33 is, for example, carried out by means of screws 34.

In the example illustrated, the cover 4 is presented in the form of a truncated pyramid and is surmounted on a covering 35, for example, of hemispheric shape.

A gap 36 is advantageously provided between the perimeter of the covering 35 and the cover 4.

This gap 36 can, first, form an air inlet to supply with fresh air, the blower(s) 7.

The gap 36 can, then, form a passage for the light emitted by an operating indicator light of the ioniser 1, for example, a light-emitting diode 37 (LED) mounted on the electronic control board 21.

According to a preferred embodiment illustrated in FIG. 1 and FIG. 5, wherein the switching on of the ioniser 1 is carried out by a direct manual action on it, the covering 35 forms a pushbutton coupled with the switch 26. The actuation of the covering 35 (by simply pressing of the finger or of the hand) makes it possible, by way of the rod 27 of the switch 26 to open or to close the circuit for electrically supplying the generator 15 and the blower(s). According to an embodiment illustrated in FIG. 5, the covering 35 is inserted with force on the rod 27, which thus ensures the support of it.

In operation, the (or each) rotor 8 generates a pulsed airflow through the exhaust pipe 9. The filaments 18 of the electrode 16 (supplied with high voltage by the generator 15) generate electrical discharges (corona discharge) accompanied by a production of ions in a large quantity. These ions are removed by the airflow and ejected outside of the ioniser 1 through perforations 6 of the cover 4.

To increase the scope of the ioniser 1, i.e. the distance at which the ions are projected, the ioniser 1 comprises, fifth, and for each blower 7, a diffuser 38.

This diffuser 38 is provided:

With a pipe 39 which extends into the extension of the exhaust pipe 9 and delimits a compression chamber 40, and With an expander 41 which extends the pipe 39 and comprises a series of channels 42 which extend from an inner face 43 of the expander 41 adjoining the compression chamber 40 to an opposite outer face 44.

In the example illustrated, the diffuser 38 is a one-piece part, preferably made of a plastic material.

The pipe 39 has an identical or complementary cross-section of the exhaust pipe 9. In the example illustrated, the pipe 39 thus has a rectangular (or square) cross-section.

The diffuser 38 can be fixed directly on the box of the blower 7. In the example illustrated, the diffuser 38 is provided with a male nozzle 45 which protrudes from the pipe to be inserted with force (or with snap-fitting) in the exhaust pipe 9.

As illustrated in FIG. 2, the diffuser 38 and/or the blower 7 is (are) provided with a notch 46 to make it possible for the mounting (FIG. 2) and the passage (FIG. 3) of the electrode 16, such that the cluster of filaments 18 extends to the right of the exhaust pipe 9. In the example illustrated, the diffuser 38 and the box 10 of the blower 7 are both provided with complementary notches 46 which, once the diffuser 38 is mounted on the box 10, jointly form an opening 47 through which the electrode 16 passes, of which the filaments 18 thus extend to the junction between the exhaust pipe 9 and the pipe 39.

In the example illustrated (see, in particular, FIG. 3), there are nine channels 42, but this number is only illustrative. There could be fewer, or more channels 42.

The channels 42 will preferably be deviated from one another from the inner face 43 of the expander 41 to the outer face 44 thereof. The sum of the cross-sections for the passage of the channels 42 is less than the cross-section for the passage of the exhaust pipe 9 (and of the pipe 39). Consequently, the air is compressed in the compression chamber 40, upstream of and in the vicinity of the inner face 43 of the expander 41.

It results that the speed of displacement of the air (charged with ions) is greater in the channels 42 that the speed of displacement of the air in the exhaust pipe 9 (the flowing of the air is illustrated by white arrows in FIG. 5).

In other words, the diffuser 38 provides, in the expander 41, an acceleration of the airflow entering through the inner face 43. It results that the ions are projected outside of the ioniser 1 at a distance greater than the distance at which they would be projected without the diffuser 38. The scope (and therefore the effectiveness) of the ioniser 1 of it is increased.

Furthermore, according to a preferred embodiment, each channel 42 which be narrowed from the inner face 43 of the expander 41 to the outer face 44 thereof, which also increases the acceleration effect of the flow and therefore the scope of the ioniser 1.

The perforations 6 in the cover 4 extend at least to the right of the (or of each) diffuser 38. It will be ensured that each channel 42 opens to the right of a perforation 6, so as to minimise the rebounds of the exiting airflow. In the example illustrated, perforations 6 are provided over the whole surface of the cover 4.

The outer face 44 of the expander extends preferably as close as possible to the cover 4. According to a preferred embodiment, the outer face 44 of the expander 41 moulds the inside of the cover 4.

To increase the density of ions produced at the level of the filaments 18, the ioniser 1 can comprise a metal ring 48 surrounding the free end 17 of the electrode 16.

This ring 48, maintained at a zero potential, forms an electrical earth which provides a gain effect by increasing the number of electrical discharges (and therefore the formation of ions) at the level of the free end 17 of the electrode 16.

According to a preferred embodiment illustrated in FIG. 2 and FIG. 3, the metal ring 48 has a flared portion 49 which surrounds the cluster of filaments 18 of the electrode 16. This flared portion 49 has the function of moulding the cluster of filaments 18, which indeed tend to be deviated from one another. According to an embodiment illustrated as a solid line in FIG. 2, the flared portion 49 of the ring is conical. According to another embodiment, illustrated as a dotted line in FIG. 2, the flared portion 49 is pyramidal (with a polygonal base) and has any number of faces (although greater than or equal to three).

The metal ring 48 is advantageously crimped on the electrode 16. As illustrated in FIG. 3, the metal ring 48 is preferably inserted in the opening 47. The metal ring 48 can be made of copper. In a variant, the metal ring is silver on the surface. It can be presented in the form of a braid or a lattice.

The invention claimed is:

1. A device for ionising air, which comprises a case and, in said case:
    a blower, which comprises a rotor to generate a pulsed airflow and an exhaust pipe to channel the pulsed airflow;
    a device for producing ions, which comprises:
        a high-voltage electrical generator;
        at least one electrode connected to the generator and of which a free end formed of a cluster of filaments made of conductive material, extends to the right of the exhaust pipe to release ions there by corona discharge;
    the device further comprising
    a diffuser provided:
        with a pipe which extends into the extension of the exhaust pipe and delimits a compression chamber, and
        with an expander which extends the pipe and comprises a series of channels which extend from an inner face of the expander adjoining the compression chamber to an opposite outer face, and
    a metal ring surrounding the free end of the electrode.

2. The device according to claim 1, wherein the channels will be deviated from one another from the inner face of the expander to the outer face thereof.

3. The device according to claim 1, wherein each channel will be narrowed from the inner face of the expander to the outer face thereof.

4. The device according to claim 1, wherein the metal ring has a flared portion which surrounds the cluster of filaments of the electrode.

5. The device according to claim 1, wherein the metal ring is crimped on the electrode.

6. The device according to claim 1, wherein the metal ring is made of copper.

7. The device according to claim 1, wherein the metal ring is silver on the surface.

8. The device according to claim 1, wherein the case comprises a base and a cover provided with perforations at least to the right of the diffuser.

9. The device according to claim 1, further comprising an electronic control board provided with a switch for opening or closing a circuit for electrically supplying the generator, and wherein the case is provided with a pushbutton coupled with the switch.

\* \* \* \* \*